United States Patent
Hashimoto et al.

(10) Patent No.: US 8,928,315 B2
(45) Date of Patent: Jan. 6, 2015

(54) EDDY CURRENT FLAW DETECTION PROBE

(75) Inventors: Mitsuo Hashimoto, Goshogawara (JP);
Hisakazu Mori, Niihama (JP);
Hidehiko Suetsugu, Niihama (JP);
Toyokazu Tada, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 475 days.

(21) Appl. No.: 13/203,795

(22) PCT Filed: Mar. 11, 2010

(86) PCT No.: PCT/JP2010/054621
§ 371 (c)(1),
(2), (4) Date: Aug. 29, 2011

(87) PCT Pub. No.: WO2010/104213
PCT Pub. Date: Sep. 16, 2010

(65) Prior Publication Data
US 2012/0007596 A1   Jan. 12, 2012

(30) Foreign Application Priority Data

Mar. 11, 2009  (JP) ................................ 2009-057571
May 8, 2009   (JP) ................................ 2009-113360
May 15, 2009  (JP) ................................ 2009-118402

(51) Int. Cl.
*G01N 27/82*    (2006.01)
*G01N 27/90*    (2006.01)

(52) U.S. Cl.
CPC .......... *G01N 27/902* (2013.01); *G01N 27/9033* (2013.01); *G01N 27/904* (2013.01)
USPC ........... 324/240; 324/220; 324/221; 324/232; 324/238

(58) Field of Classification Search
USPC ......................................................... 324/220
See application file for complete search history.

(56) References Cited

U.S. PATENT DOCUMENTS 3,449,662 A    6/1969  Wood
3,952,314 A *  4/1976  Maltz ........................ 346/140.1
(Continued)

FOREIGN PATENT DOCUMENTS

JP  7-218473 A    8/1995
JP  08027260 B2 * 3/1996
JP  8-193981 A    7/1996

OTHER PUBLICATIONS

Machine English translation of Japanese Patent Application Publication to Inventor Yoshihisa Shindo. JP 08-027260 B2, Mar. 21, 1996. Translation of pp. 2-5 created on Sep. 25, 2013.*

(Continued)

*Primary Examiner* — Melissa Koval
*Assistant Examiner* — Stephen G Armstrong
(74) *Attorney, Agent, or Firm* — Birch, Stewart, Kolasch & Birch, LLP

(57) ABSTRACT

An insertion type eddy current flaw detection probe capable of more accurately detecting flaws in magnetic tubes is provided. A method for inspecting magnetic tubes for flaws with high accuracy is also provided. A eddy current flaw detection probe contains a cylindrical yoke (1), a plurality of detection coils (5) disposed around the central portion of the cylindrical yoke in the direction of a cylindrical axis thereof, first and second inner excitation coils (6) disposed on both sides of the plurality of detection coils in the direction of the cylindrical axis, and first and second permanent magnets (3, 4) disposed around the yoke on both sides of the first and second excitation coils in the direction of the cylindrical axis so that the direction of magnetizations thereof are parallel to the radial direction of the yoke and magnetic poles on the cylindrical yoke side thereof are different from each other.

9 Claims, 8 Drawing Sheets

(56) References Cited

U.S. PATENT DOCUMENTS 3,952,315 A * 4/1976 Cecco ............................ 324/220
4,189,944 A * 2/1980 Day et al. ......................... 73/623

OTHER PUBLICATIONS

International Search Report, dated Aug. 5, 2010, issued in PCT/JP2010/054621.
Sakamoto et al., "Eddy Cement Examination Using Inner Coil with Strongly Magnetizing Efficiency for Duplex Stainless Steel Tubes", Journal of Non-Destructive Inspection, ISSN 0367-5866, vol. 42, pp. 520-526, Jan. 1, 1993.
Notification of Reasons for Rejection for corresponding Japanese Patent Application No. 2009-11360, dated Sep. 11, 2012.
Notification of Reasons for Rejection for corresponding Japanese Patent Application No. 2009-118402, dated Dec. 4, 2012.
Notification of Reasons for Rejection for corresponding Japanese Patent Application No. 2009-118402, dated Sep. 11, 2012.
The First Office Action, dated Oct. 28, 2013, in the corresponding Chinese Patent Application No. 201080011030.2.

* cited by examiner

US 8,928,315 B2

EDDY CURRENT FLAW DETECTION PROBE

TECHNICAL FIELD

The present invention relates to an eddy current flaw detection probe, and in particular to an insertion type eddy current flaw detection probe suitable for detecting flaws in magnetic tubes.

The present invention also relates to a method for inspecting magnetic tubes for flaw with high accuracy.

BACKGROUND ART

Among methods for inspecting metallic materials is the eddy current flaw detection. The eddy current flaw detection by means of the insertion type eddy current flaw detection probe is widely employed in the inspection of non-magnetic tubes made of such metals as austenitic stainless steel, titanium or copper alloy.

When inspecting a magnetic tube made of carbon steel, ferritic stainless steel, duplex phase stainless steel (or tow-phase stainless steel) consisting of ferrite phase and austenite phase or the like, flaws cannot be detected accurately since the eddy current flaw detection probe for non-magnetic tubes causes eddy currents to flow only in the surface and sensitivity of the detector is adversely affected by a noise attributable to local variation in magnetic permeability.

A known eddy current flaw detection probe for duplex phase stainless steel heat transfer tube has such a constitution as detection coils are disposed around a central portion of a cylindrical yoke in the direction of the cylindrical axis thereof, and permanent magnets are disposed around the yoke on both sides of the detection coil in the direction of the cylindrical axis so that the direction of magnetization lies in the radial direction of the yoke and the magnetic poles on the yoke side are different from each other (refer to, for example, Non-Patent Document 1).

While use of this probe enables eddy current flaw detection for a weakly magnetic tube such as duplex phase stainless steel tube, it is not sensitive enough to detect small flaws in a ferromagnetic tube made of carbon steel or the like. Thus there is a demand for a method capable of accurately detecting small flaws in ferromagnetic tubes.

A magnetic body having relatively low saturation magnetic flux density such as 0.5 tesla or less may refer to weakly magnetic body herein and a magnetic body having relatively high saturation magnetic flux density such as 1.6 tesla or higher may refer to ferromagnetic body herein.

PRIOR ART DOCUMENT

Non-Patent Document 1: "Nondestructive Inspection", Vo. 42, No. 9, pp. 520-526, 1993

SUMMARY OF INVENTION

Technical Problem

An object of the present invention is to provide an insertion type eddy current flaw detection probe that is capable of accurately detecting flaws in magnetic tubes.

Another object of the present invention is to provide a method for inspecting magnetic tubes for flaws with high accuracy, and particularly a method for accurately detecting flaws in a magnetic tube in a portion of baffle plate, tube plate, support rig and the like (hereinafter referred to simply as baffle) provided outside of the magnetic tube.

Solution to Problem

Through researches into the method of eddy current flaw detection for magnetic tubes, the inventors of the present application found that flaws in magnetic tubes can be detected more accurately by applying eddy current flaw detection using a probe having such a constitution as detection coils are disposed around a central portion of a cylindrical yoke, inner excitation coils are disposed on both sides of the detection coils, and permanent magnets are disposed around the yoke on both sides of the excitation coils so that the directions of magnetization thereof lie in the radial direction of the yoke and magnetic poles on the yoke side are different from each other.

"Detection coils are disposed around a central portion of a cylindrical yoke" as used herein refers to that detection coils are disposed around a cylindrical yoke at the central portion of the cylindrical yoke in the direction of the axis (cylindrical axis) of the cylindrical yoke. In general a flaw detection signal is obtained by means of a differential method in which the differences in signals from two or more detection coils are used and thus in this case a plurality of detection coils (two or more detection coils) are disposed.

"Inner excitation coils are disposed on both sides of the detection coils" used as herein refers to that each excitation coil is disposed on each side of both sides of the detection coils in the direction of the cylindrical axis and thus, two excitation coils in total are disposed.

"Permanent magnets are disposed around the yoke on both sides of the excitation coils so that the directions of magnetization thereof lie in the radial direction of the yoke and magnetic poles on the yoke side are different from each other" used herein refers to that each permanent magnet is disposed on each side of both sides (outsides) of the excitation coils in the direction of the cylindrical axis and thus two permanent magnets in total are disposed, and that the directions of magnetization of the two permanent magnets are in the radial direction of the cylindrical yoke and magnetic poles on the cylindrical yoke side are different from each other (i.e. the directions of magnetization are opposite each other).

These references can be applicable to other embodiments described below.

Thus the present invention provides the eddy current flaw detection probe comprising a cylindrical yoke, a plurality of detection coils disposed around the central portion of the cylindrical yoke in the direction of a cylindrical axis thereof, first and second inner excitation coils disposed on both sides of the plurality of detection coils in the direction of the cylindrical axis, and first and second permanent magnets disposed around the yoke on both sides of the first and second excitation coils in the direction of the cylindrical axis so that the direction of magnetizations thereof are parallel to the radial direction of the yoke and magnetic poles on the cylindrical yoke side thereof are different from each other.

Through researches into the eddy current flaw detection for magnetic tubes, the inventors of the present application devised another present invention by finding that flaws in magnetic tubes can be detected more accurately by applying eddy current flaw detection method using a probe that has such a constitution as detection coil is disposed around a central portion of a cylindrical yoke and permanent magnets are disposed around the yoke on both sides of the detection coil so that the directions of magnetization lie in the radial direction of the yoke and magnetic poles on the yoke side are different from each other, wherein a permanent magnet is further mounted in the central portion of the probe so that the direction of magnetization lies in axial direction (the direction of the cylindrical axis) of the yoke.

Thus another present invention provides the eddy current flaw detection probe having such a constitution as permanent magnet is disposed around the central portion of the cylindrical yoke so that the direction of magnetization thereof lies in the axial direction of the yoke, permanent magnets are disposed around the yoke on both sides of the former permanent magnet so that the directions of magnetization thereof lie in the radial direction of the yoke and magnetic poles on the yoke side are different from each other, and a detection coil is disposed on the permanent magnet that is located in the central portion.

Through researches into the eddy current flaw detection for magnetic tubes, the inventors of the present application devised yet another present invention by finding that flaws in magnetic tubes can be detected more accurately by applying eddy current flaw detection method to the inside of the magnetic tubes using a probe that has such a constitution as detection coil is disposed around a central portion of a cylindrical yoke and permanent magnets are disposed around the yoke on both sides of the detection coil so that the directions of magnetization lie in the radial direction of the yoke and magnetic poles on the yoke side are different from each other, wherein a permanent magnet is further mounted in the central portion of the probe so that the direction of magnetization lies in axial direction of the yoke, and also that flaws of the magnetic tube in portions of baffle provided in the outside can also be accurately inspected by applying the eddy current flaw detection employing multiple frequency method.

Thus yet another present invention provides (1) a flaw detection method for magnetic tubes wherein eddy current flaw detection in the inside of a magnetic tube is carried out by using the probe having such a constitution as permanent magnet is disposed around the central portion of the cylindrical yoke so that the direction of magnetization thereof lies in the axial direction of the yoke, further permanent magnets are disposed around the yoke on both sides of the former permanent magnet so that the directions of magnetization thereof lie in the radial direction of the yoke and magnetic poles on the yoke side are different from each other, and a detection coil is disposed on the permanent magnet that is located in the central portion; and (2) a method of eddy current flaw detection based on multiple frequency method in the flaw detection method for magnetic tubes (1).

Advantageous Effects of Invention

Use of the probes of the present inventions in eddy current flaw detection of magnetic tubes makes it possible to detect flaws more accurately.

The method of the present invention makes it possible to detect flaws in magnetic tubes accurately, and also accurately detect flaws in the magnetic tube in the portion of baffle provided outside of the magnetic tube.

DESCRIPTION OF EMBODIMENTS

Figure 1:
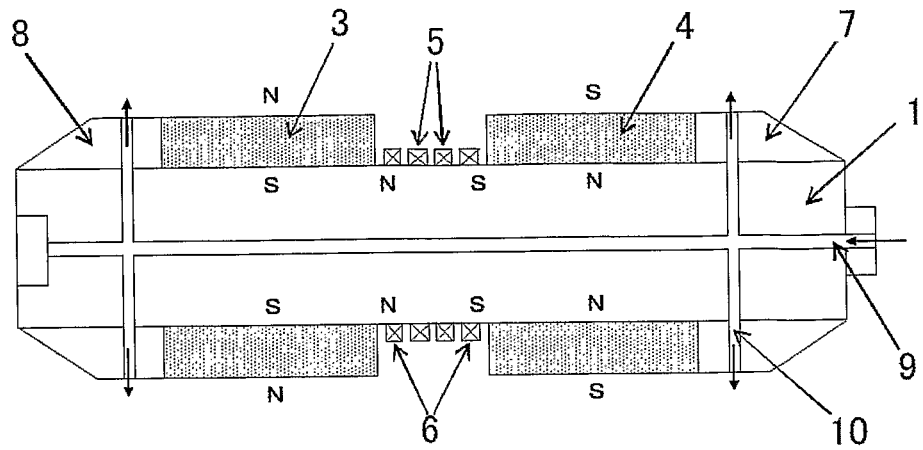
FIG. 1 is a schematic sectional view showing an embodiment of the probe of the present invention.

The present invention will be described in detail below with reference to the accompanying drawings. FIG. 1 is a schematic sectional view showing an embodiment of the probe of the present invention.

Detection coils 5 and inner excitation coils 6 (i.e. two inner excitation coils of first and second inner excitation coils 6) located on both sides of the former (i.e. both sides (both outsides) of two detection coils 5 in the direction of a cylindrical yoke 1) are disposed around a central portion of a cylindrical yoke 1 (i.e. around a central portion of a cylindrical yoke 1 in the direction of the cylindrical yoke 1). A permanent magnet 3 (a first permanent magnet) and a permanent magnet 4 (a second permanent magnet) are disposed around the yoke on both sides of the coils (i.e. around portions of the cylindrical yoke 1 located at both sides (both outsides) of the two inner excitation coils 6 in the direction of the cylindrical axis of the cylindrical yoke 1), so that the direction of magnetization thereof lies in the radial direction of the yoke and the magnetic pole on the yoke side is different between the permanent magnet 3 and the permanent magnet 4. In the configuration shown in FIG. 1, the permanent magnet 3 is disposed so that the S pole is located on the yoke side and the N pole is located on the outside, and the permanent magnet 4 is disposed so that the N pole is located on the yoke side and the S pole is located on the outside.

In many cases two detection coils 5 are disposed as shown in FIG. 1 because high accuracy of a flaw detection process can be achieved by using coils differentially connected by which an output difference between two coils can be detected. However, the present invention is not limited to this.

Figure 2:
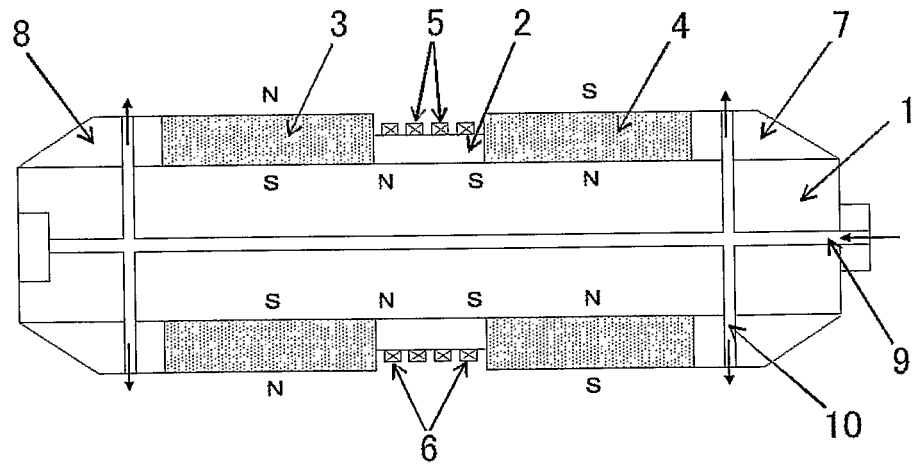
FIG. 2 is a schematic sectional view showing another embodiment of the probe of the present invention.

When a plurality of detection coils 5 are used, preferably two internal excitation coils 6 are disposed as shown in FIG. 2 so that the excitation coils 6 are located at the both sides (outsides) of the plurality of detection coils 5 in the axis direction of the yoke 1.

Guides 7, 8 are provided on both ends of the probe. An air intake hole 9 is provided in substantially the central portion of the yoke 1 (i.e. extending in the substantial center of the cylindrical yoke 1 to the direction of the cylindrical axis), and a plurality of air discharge holes 10 are provided on both ends so as to extend from the air intake hole in the radial direction (i.e. air discharge holes 10 extending from the air intake hole 9 to the surface of the cylindrical yoke 1 in the radial direction of the cylindrical yoke 1).

Lead wires of the coils and lead-out holes thereof are not shown.

FIG. 2 is a schematic sectional view showing another embodiment of the probe of the present invention.

In the embodiment shown in FIG. 2, a permanent magnet (third permanent magnet) is disposed around a central portion of a cylindrical yoke 1, so that the direction of magnetization lies in the axial direction of the yoke. In the configuration illustrated, the permanent magnet is disposed so that the N pole is positioned at the left and the S is positioned at the right.

A permanent magnet 3 and a permanent magnet 4 are disposed around the yoke on both sides of the permanent magnet 2, so that the directions of magnetization thereof lie in the radial direction of the yoke and the magnetic pole on the yoke side is different between the permanent magnet 3 and the permanent magnet 4. In the configuration illustrated, the permanent magnet 3 is disposed so that the S pole is positioned on the yoke side and the N pole is positioned on the outside, and the permanent magnet 4 is disposed so that the N pole is positioned on the yoke side and the S pole is positioned on the outside.

Detection coil 5 is disposed on the permanent magnet 2 located in the central portion. Internal excitation coils (or magnetic field compression coils) 6 are disposed on both sides of the detection coils.

Guides 7, 8 are provided on both ends of the probe. An air intake hole 9 is provided in substantially the central portion of the yoke 1, and a plurality of air discharge holes 10 are provided on both ends so as to extend from the air intake hole in the radial direction.

Lead wires of the coil and lead-out holes thereof are not shown in FIG. 2 either.

That is, the probe according to the embodiment shown in FIG. 2 is the same as that of the embodiment shown in FIG. 1, except that a permanent magnet 2 is mounted between the cylindrical yoke 1 and the detection coils 5, the inner excitation coils 6 (or between cylindrical yoke 1 and the detection coils 5 and between the cylindrical yoke 1 and the inner excitation coils 6), so that direction of magnetization of the permanent magnet 2 agrees with the axial direction of the yoke.

A prove according to the embodiment shown in FIG. 1 or FIG. 2 except for that the inner excitation coils 6 are disposed on the permanent magnet 3 in the vicinity of the inner end (the inner end in the direction of the cylindrical axis) thereof and disposed on the permanent magnet 4 in the vicinity of the inner end (the inner end in the direction of the cylindrical axis) thereof.

The lengths of the permanent magnets 3, 4 in the direction of the cylindrical axis are larger than those or the inner excitation coils 6, and thus when the excitation coils 6 are disposed on the permanent magnets 3, 4 in the vicinity of the inner ends thereof, part of the permanent magnet 4 and part of the permanent magnet 3 are located at both sides (outsides) of the inner excitation coils 6 in the direction of the cylindrical axis. In addition, the inner excitation coils 6 disposed as described are located at both sides (outsides) of the detection coils 6.

The yoke 1 of the probe shown in FIGS. 1 and 2 may be formed from a metal having high permeability such as carbon steel or low-alloy steel.

For the permanent magnet, high performance permanent magnet such as neodymium magnet is used. For the permanent magnet 2 mounted in the central portion, a ring-shaped magnet about 5 to 10 mm long in the axial direction of the yoke is used. For the permanent magnet 3 and the permanent magnet 4 mounted on both sides of the permanent magnet 2, ring-shaped magnets about 5 to 30 mm, preferably about 10 to 30 mm long in the axial direction of the yoke are used. While the accuracy of flaw detection becomes higher as the permanent magnet 3 and the permanent magnet 4 become longer, similar effect cannot be achieved by increasing the length beyond 30 mm. Sizes of the permanent magnet 3 and the permanent magnet 4 in the radial direction of the yoke and thickness of the magnets may be changed in accordance to the thickness of the magnetic tube to be inspected.

The permanent magnet 2 disposed in the central portion makes it possible to increase the magnetic flux density of the magnetic field generated by these magnets. Thus the probe according to the present invention preferably comprises the permanent magnet 2 although alternatively magnetic flux density can be increased by reducing the distance between permanent magnet 3 and permanent magnet 4. By setting the direction of magnetization of the permanent magnet 2 so that the N pole is positioned at the left and the S pole is positioned at the right as shown in FIG. 2, is made possible to increase the magnetic flux density. However even when N pole is positioned at the right and the S pole is positioned at the left sufficient performance of flaw detection can be obtained.

This means that it does not matter on which side N pole (or S pole) is located and as log as the direction of magnetization lies in the direction of the cylindrical axis of the yoke 1 (the axial direction of the yoke 1).

When differentially connected coils employing only the detection coils 5 which have conventionally been used are employed, the region where eddy currents are induced becomes too large, and therefore the S/N ratio decreases under the influence of local variation of permeability in a portion where magnetization has not saturated. According to the present invention, in contrast, excessive region of eddy currents induced by the detection coils 5 is restricted by canceling the eddy current by the eddy current that is induced to flow in the opposite direction by the inner excitation coils 6 which are disposed on the outside of the detection coils, thereby improving the S/N ratio.

As the result of improving the S/N ratio by making the magnetic flux distribution uniform by means of the permanent magnet 2 and inducing the eddy currents only in the vicinity of the detection coils 5 by the inner excitation coils 6, in addition to the improvement in the sensitivity of flaw detection, it is made possible to detect the phase angle that relates to the type of flaw (circumferential groove in the inner or outer surface, rectangular groove on the outside, or through hole) and depth of the flaw, and identify the flaw located in the tube below baffle, by employing multiple frequency method.

The magnetic flux density of the magnetic field generated by these magnets is preferably 1.5 tesla or higher in the central portion between the detection coils. A magnetic flux density lower than 1.5 tesla results in weaker flaw detection signal, and is therefore not desirable.

The magnetic flux density mentioned in the present invention is a value determined by numerical analysis of finite element method with a magnetic field analysis program "Magnetic Field Analysis Software JMAG" (registered trade mark) available from JSOL Corporation.

Figure 3:
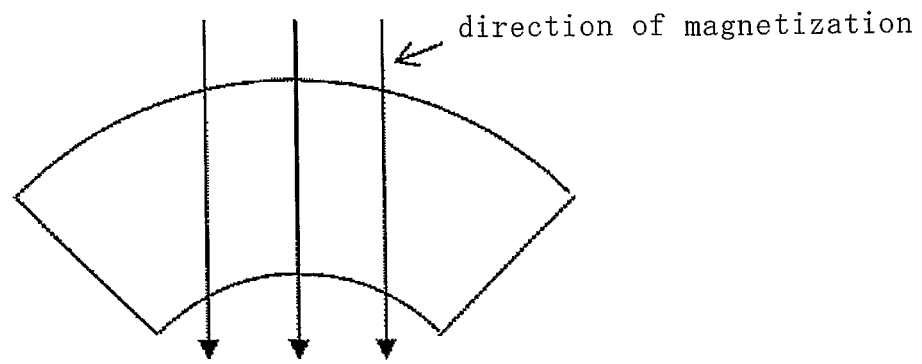
FIG. 3 is a schematic diagram showing a method for mounting permanent magnets in the probe of the present invention.
Figure 4:
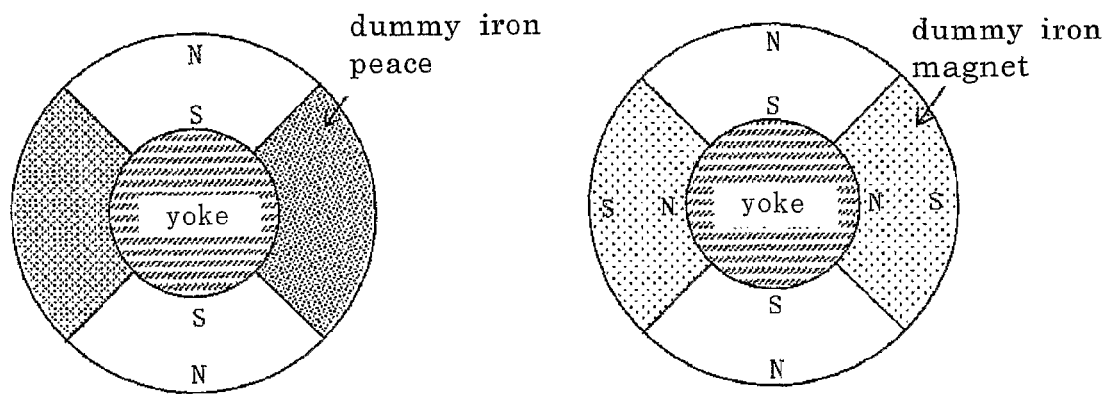
FIG. 4 is a schematic diagram showing a method for mounting permanent magnets in the probe of the present invention.
Figure 5:
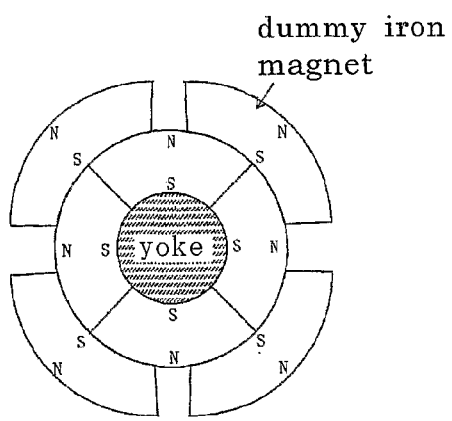
FIG. 5 is a schematic diagram showing a method for mounting permanent magnets in the probe of the present invention.

A ring-shaped permanent magnet that causes magnetization in the radial direction requires high manufacturing cost, and therefore it is a common practice to split the magnet into split shapes such as quadrants which are disposed around a cylindrical yoke as shown in FIG. 3. When mounting the permanent magnet split into four parts along the circumference around the cylindrical yoke, dummy iron pieces or permanent magnets (dummy magnet as shown in FIG. 4) that have direction of magnetization opposite to that of the permanent magnet to be mounted is interposed between the quadrants as shown in FIG. 4, so that the repulsion force of the opposing permanent magnets is canceled out thereby making it easier to mount. While there is no restriction on the method of mounting the permanent magnets around the cylindrical yoke, an adhesive such as acrylic adhesive is used for bonding. After mounting a pair of permanent magnets, the dummy iron pieces or the permanent magnets that have the direction of magnetization opposite to that of the permanent magnet to be mounted are removed and, in place thereof, another pair of permanent magnets with adhesive applied to the surface thereof that makes contact with the cylindrical yoke are mounted, while the opposing permanent magnets are held in place by a vise or the like till the adhesive has been cured, thereby making it easy to mount the permanent magnets on the cylindrical yoke. In another method, permanent magnets that cause magnetization in the radial direction are arranged via an adhesive around the cylindrical yoke, and dummy permanent magnets having opposite direction of magnetization are mounted so as to cover the permanent magnet and straddle over adjacent permanent magnets, as shown in FIG. 5. This scheme mitigates the repulsion force and makes it possible to easily bond the permanent magnets onto the cylindrical yoke without need to secure the permanent magnets by vise or the like. The dummy permanent magnets may be removed after the adhesive has been hardened.

When split shaped magnets are used as the permanent magnets 3 and 4, the split shaped magnets are preferably disposed symmetrical with respect to the central axis of the cylindrical yoke 1 as shown in FIG. 4.

Whole circumference of the magnetic tube can be substantially uniformly magnetized by the symmetrical arrangement.

The two detection coils 5 and the two inner excitation coils 6 are formed by winding copper wires having a diameter of about 0.05 to 0.1 mm about 60 to 80 turns to form the coil measuring about 0.8 to 1.2 mm in width and about 0.8 to 1.2 mm in depth.

The inner excitation coils restrict the region where eddy currents flow to the vicinity of flaw, so as to improve the S/N ratio of signal from a small flaw and reduce the influence of the ends of the tube.

The guides 7, 8 disposed on both ends of the probe are formed from an acetal resin, a stainless steel or the like, and are secured onto the yoke by screws.

Air is introduced through the air intake hole 9 provided in the yoke 1 and is discharged through the air discharge hole 10. When testing a magnetic tube, it becomes difficult to scan and center the probe since the strong permanent magnet mounted on the probe is attracted toward the tube surface. However, attraction toward the tube surface is mitigated by ejecting air from the air discharge holes in the perpendicular direction, thus making it easier to scan the probe.

About 6 to 10 air discharge holes 10 having a diameter of about 2 mm may be arranged in the circumferential direction to run from the air intake hole 9.

The coils are connected by lead wires to an eddy current flaw detection apparatus, to measure time-voltage characteristic and detect flaws.

Figure 6:
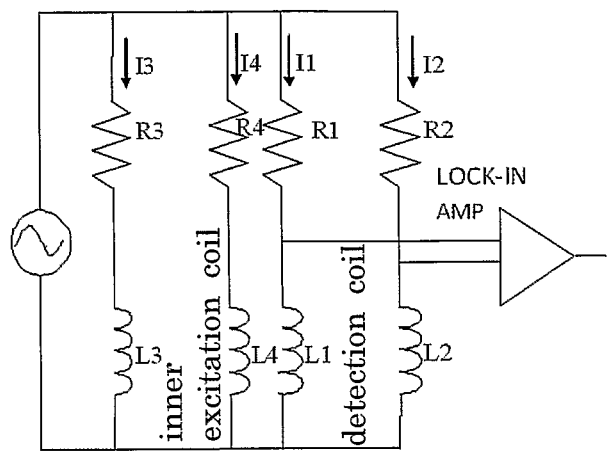
FIG. 6 is a circuit diagram of the probe of the present invention.

FIG. 6 shows a circuit diagram of the probe. Two detection coils L1, L2, two inner excitation coils L3, L4 and four variable resistors R1, R2, R3, R4 are connected in parallel with a lock-in amplifier, and the detection coils L1, L2, and the variable resistors R1, R2 are connected to the signal input terminals of the lock-in amplifier so as to form a Wheatstone bridge.

Flaw detection operation is carried out as follows.

When a voltage of 5 V is applied with a predetermined test frequency, for example 100 kHz at which sensitivity of flaw detection becomes high, impedances of the detection coils and the inner excitation coils are measured and the variable resistors R1 and R2 are adjusted to resistances that match the measured impedances. Composite impedance (synthetic impedance) of the detection coils and the variable resistors is measured at this time, and the resistances of the variable resistors R3, R4 that are connected to the inner excitation coils are varied around the measured resistance, so as to carry out flaw detection under conditions that allow high sensitivity of detection.

Scan velocity of the probe is set in a range from about 2 to 50 mm/sec., and is preferably in a range from about 2 to 10 mm/sec. in order to detect smaller flaws accurately.

The method described above makes it possible to detect flaws accurately in a portion of magnetic tube where baffle is not provided outside of the magnetic tube, although it is not possible to detect flaws of the magnetic tube accurately in a portion where baffle is provided due to the interference of the signal from the baffle.

For the purpose of eliminating the interfering signals so as to improve the accuracy of eddy current flaw detection, there is known the multiple frequency method wherein a current having two or more frequencies is provided with the detection coils in the eddy current flaw detection. The multiple frequency method is according to, for example, "Eddy Current Flaw Detection II" of Non-destruction Inspection Series, sixth issue of 1995 version published by Japan Non-destruction Inspection Association on Oct. 5, 2002.

Description that follows deals with flaw detecting operation for a magnetic tube in a portion where a baffle is provided by employing the multiple frequency method using two frequencies. FIG. 4 is a diagram explanatory of this operation.

Figure 7:
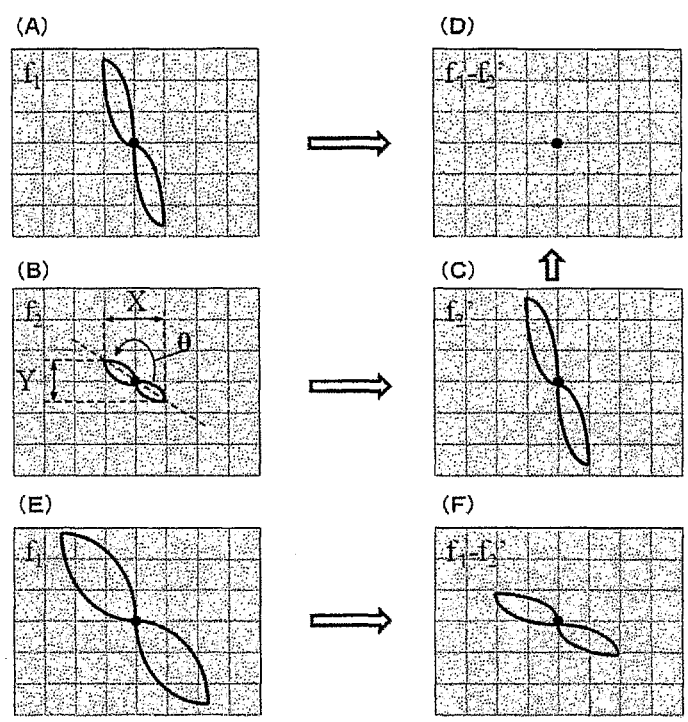
FIG. 7 is a diagram explanatory of multiple frequency method.

Flaw detection with frequency $f_1$ in a flawless magnetic tube of a portion where a baffle is provided produces such a signal from the baffle (Lissajous curve) as shown in FIG. 7(A) ($f_1$ operation). Flaw detection with the frequency changed to $f_2$ produces such a signal from the baffle as shown in FIG. 7(B) ($f_2$ operation). Amplitudes X, Y and phase θ of the baffle signal obtained with frequency $f_2$ are rotated so as to make the amplitude and inclination of the signal as close to those of the baffle signal obtained during flaw detection with frequency $f_1$ as possible (FIG. 7 (C)). This operation will be referred to as $f_2'$ operation since it is adjustment of the signal obtained with frequency $f_2$.

When an operation ($f_1-f_2'$) in which the signal of $f_2'$ operation is subtracted from the signal of $f_1$ operation is conducted, the baffle signal is canceled out because both signals have similar Lissajous curves (FIG. 7 (D)).

Flaw detection with frequency $f_1$ in a magnetic tube that has flaw in a portion where the baffle is provided produces such a signal as shown in (E) that is composite of baffle signal and flaw signal (f1 operation). Baffle signal is eliminated through an operation ($f_1-f_2'$) similar to that described above, so as to extract only the flaw signal without the baffle signal (FIG. 7(F)), and the presence of flaw is inspected through comparison with FIG. 7(D).

In case frequencies $f_1$ and $f_2$ are close to each other, the baffle signal and the defect signal become similar and therefore the subtracting operation may result in the loss of most of the flaw signal. When the frequencies $f_1$ and $f_2$ are set too distant from each other, in contrast, basic waveforms change. As a result, baffle signals obtained in the $f_1$ operation and $f_2$ operation cannot be adjusted into similar forms and it becomes impossible to eliminate the baffle signal. It is a common practice to set the frequency $f_2$ to about ½ to ⅛ of the frequency $f_1$. The frequency varies depending on such factors as the type of material of the magnetic tube, and an optimum frequency is selected by test scanning.

Eddy current flaw detection and data processing are carried out by means of a circuit that provides the frequencies $f_1$ and $f_2$ at the same time with the detection coils and performs the data processing, and scanning the probe to search for flaws.

Eddy current flaw detection may also be carried out by providing the frequencies $f_1$ and $f_2$ separately with the detection coils and then processing the signals thus obtained.

In case flaw detection is disturbed by a spurious signal (or noise) other than the baffle signal such as probe chatter signal (a signal caused by fluctuating distance between the tube under test and the detection coil when the probe makes jittery movement), the undesired signal may be removed by using a third frequency.

EXAMPLES

The present invention will be described below by way of Examples, but the present invention is not limited to the following Examples.

Example 1

A probe same as that shown in FIG. 2 was fabricated, by using members of the following materials and shapes.
Yoke 1: Annealed carbon steel S15C
Permanent magnet 2: Neodymium magnet manufactured by Asahi Corporation
Ring shape measuring 25.5 mm in outer diameter, 21 mm in inner diameter and 6.4 mm in length
Permanent magnets 3, 4: Neodymium magnets manufactured by Asahi Corporation
Ring shape measuring 28 mm in outer diameter, 21 mm in inner diameter and 30 mm in length divided into four parts
Detection coils 5, inner excitation coils 6: Formed from a copper wire having a diameter of 0.08 mm wound 70 turns into size of 1.0 mm in width and 1.0 mm in depth, with separation of 0.8 mm between coils.
Guides 7, 8: Polyacetal (copolymer) DURACON (trademark) manufactured by Polyplastics Co., Ltd., 28.4 mm in outer diameter
Adhesive to bond the permanent magnets to the yoke: Acrylic adhesive Hardlock (trademark) manufactured by DENKI KAGAKU KOKGYO KABUSHIKI KAISHA The magnetic flux density of the magnetic field generated by the permanent magnets was determined by using a magnetic field analysis program "Magnetic Field Analysis Software JMAG" (trademark) manufactured by JSOL Corporation. The magnetic flux density obtained in the central portion between the detection coils was 2.0 tesla. When the permanent magnet 2 was mounted so that direction of magnetization would be opposite to that shown in FIG. 2, namely the S pole was positioned at the left and the N pole was positioned at the right, the magnetic flux density was 1.6 tesla in the central portion between the detection coils.

For the lock-in amplifier, LI5640 (manufactured by NF Corporation) was used, for the oscilloscope TDS3104B (manufactured by Techtronics Japan) was used and for stage controller for scanning the probe CAT-E (manufactured by Chuo Precision Industrial Co., Ltd.) was used.

Probe circuit was made as shown in FIG. 6. When a voltage of 5 V was applied with test frequency of 100 kHz, measurement of impedance of the detection coils and the inner excitation coils showed about 93Ω, and therefore resistances of the variable resistors R1 and R2 were adjusted to about 93Ω. Measurement of the composite impedance of the detection coils and the variable resistors at this time showed about 172Ω. Flaw detection was carried out while changing the resistances of the variable resistors R3 and R4 that were connected to the inner excitation coils in a range from 150 to 500Ω under this condition.

Flaw detection was carried out on a ferromagnetic tube (carbon steel STB340, 34 mm in outer diameter, 2.3 mm in thickness and 900 mm in length) having through holes of diameters 2.0 mm, 1.5 mm, 1.0 mm and 0.5 mm formed at intervals of 100 mm, while scanning at velocities of 30 mm/sec. and 4 mm/sec.

Figure 8:
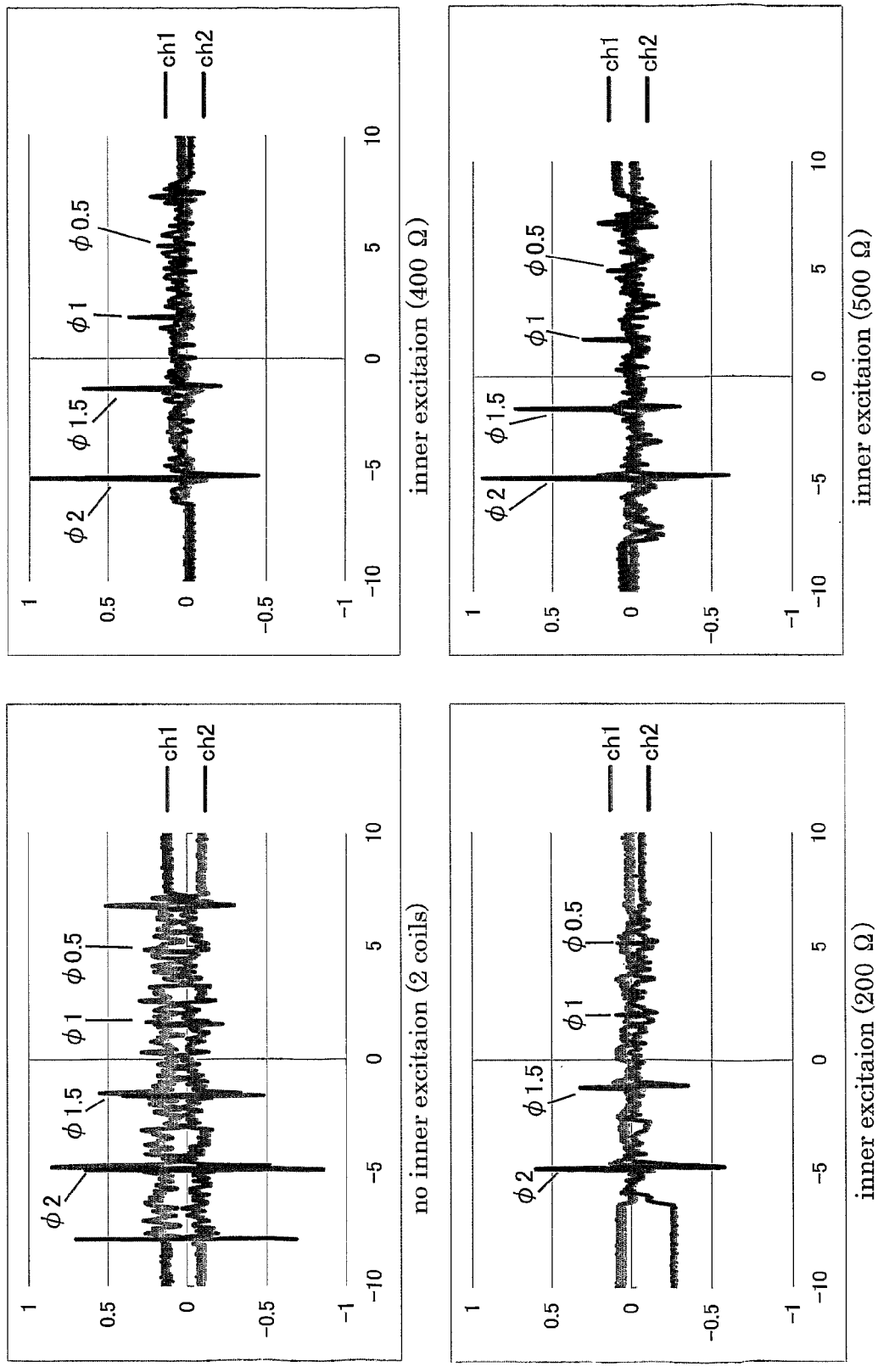
FIG. 8 shows the results of Example 1.
Figure 9:
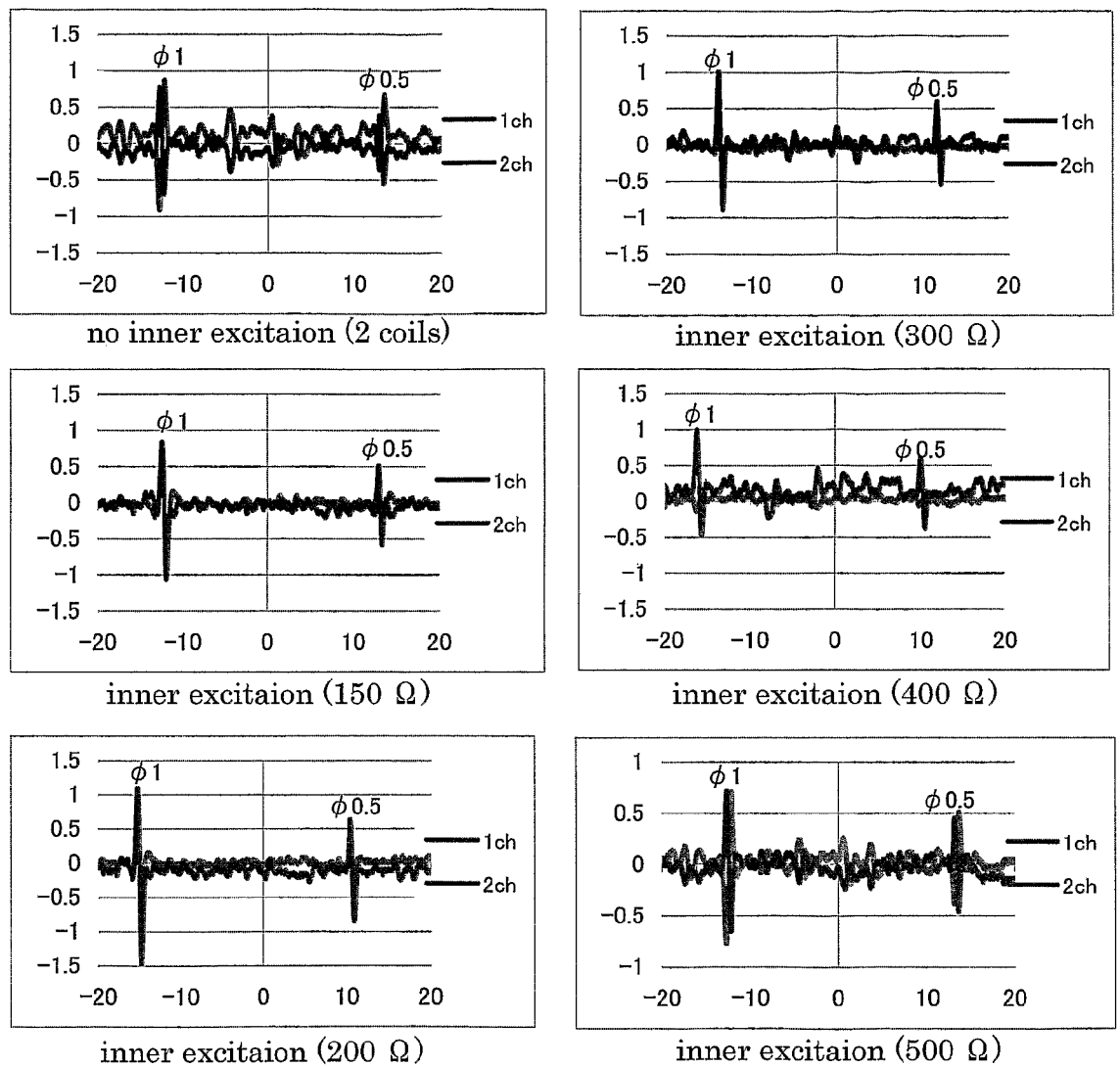
FIG. 9 shows other results of Example 1.

Result of flaw detection with scanning velocity of 30 mm/sec. is shown in FIG. 8, and result of flaw detection over the through holes of diameters 1.0 mm and 0.5 mm with scanning velocity of 4 mm/sec. is shown in FIG. 9.

In the diagram, the note "No internal excitation (2 coils)" shows that only the detection coils were used without activating the inner excitation coil in the flaw detection, and the values 150 to 500Ω are resistances of the variable resistors R3 and R4.

In the detection of small flaws of 2 mm or less in diameter, S/N ratio was obviously higher when the probe equipped with the inner excitation coils were used, than in the case of using the probe having only the detection coils without inner excitation coil. When the scanning velocity was about 4 mm/sec., absence of the inner excitation coil resulted in a low S/N ratio and inability to detect either of the through holes of diameters 1.0 mm and 0.5 mm, while the use of the probe equipped with the inner excitation coils made it possible to detect both of the through holes with sufficiently high sensitivity.

Example 2

The air intake hole 4 mm in diameter was formed inside in the axial direction of the yoke (direction of the cylindrical axis of the yoke) and eight air discharge holes 2 mm in diameter were formed to extend in the radial direction from the air intake hole on both sides (guide sections) of the permanent magnets of the probe used in Example 1.

Air was supplied through the air intake hole at a pressure controlled by a regulator and the probe was pulled so as to move at a constant speed while discharging air through the air discharge holes with a spring balance attached to an end of the probe that was inserted into the same ferromagnetic tube as that of Example 1, and the pulling force immediately before the probe started to move was measured. Measurement was made five times under the same condition, and the measurements were averaged.

Results of the measurements are shown in Table 1. It is indicated that the pulling force decreased and scanning became easier, when the air pressure was increased to discharge more air.

"Both sides of the permanent magnets" used herein refers to that outside of the permanent magnet 3 and outside of the permanent magnet 4 in the direction of the cylindrical axis of the yoke 1.

TABLE 1

| | Air pressure (Mpa) | | | | | | | |
|---|---|---|---|---|---|---|---|---|
| | 0 | 0.1 | 0.2 | 0.3 | 0.4 | 0.5 | 0.6 | 0.7 |
| Pulling force (g) | 570 | 580 | 512 | 460 | 446 | 390 | 380 | 360 |

Example 3

Artificial flaws were given to a ferromagnetic tube (carbon steel STB340 measuring 34 mm in outer diameter, 2.3 mm in thickness and 900 mm in length) by forming a through hole of diameter 1 mm, a rectangular groove measuring 5 mm in width, 12.5 mm in length and 25% of the tube thickness in depth on the outer surface, a rectangular groove measuring 5 mm in width, 17.5 mm in length and 50% of the tube thickness in depth on the outer surface, an inner circumferential groove measuring 1.5 mm in width and 20% of the tube thickness in depth, an inner circumferential groove measuring 1.5 mm in width and 70% of the tube thickness in depth, an outer circumferential groove measuring 1.5 mm in width and 50% of the tube thickness in depth and an outer circumferential groove measuring 1.5 mm in width and 80% of the tube thickness in depth.

The ferromagnetic tube was inserted into a hole of a dummy baffle (carbon steel SS400, 100 mm in length, 100 mm in width and 15 mm in thickness with a hole 34.4 mm in diameter formed at the center). Eddy current flaw detection was carried out while changing the position of the dummy baffle, by using the same probe and the same eddy current flaw detection apparatus as those of Example 1.

Flaw detection was carried out with scanning velocity set to about 4 mm/sec. and frequency $f_1$ to 20 kHz ($f_1$ operation), followed by flaw detection with frequency $f_2$ set to 10 kHz ($f_2$ operation).

Data obtained from these operations were processed by rotating the amplitudes X, Y and phase θ of the baffle signal obtained with $f_2$ operation so as to make the amplitude and inclination of the signal as close to those of the baffle signal obtained during flaw detection with $f_1$ operation as possible ($f_2'$ operation).

Figure 10:
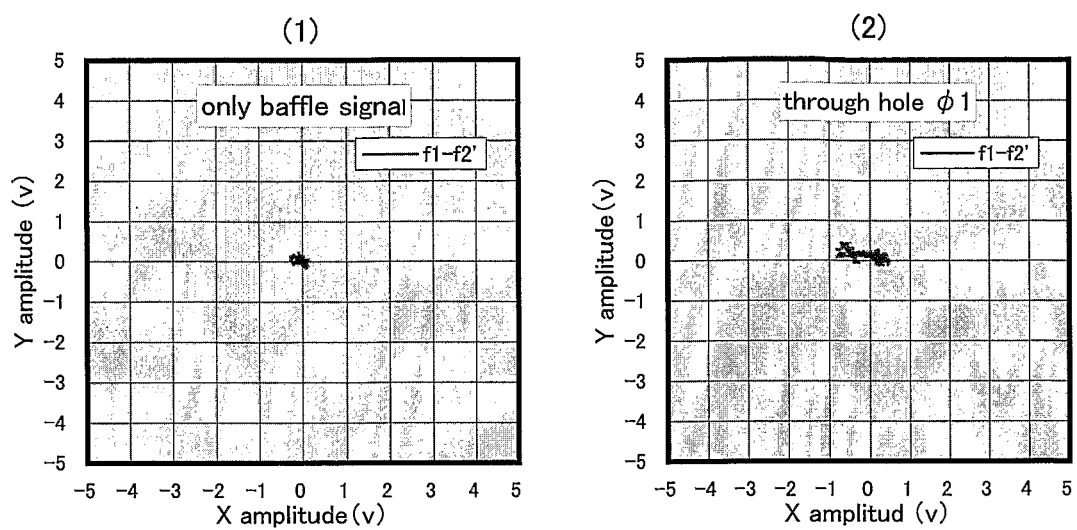
FIG. 10 shows the results of Example 3.
Figure 11:
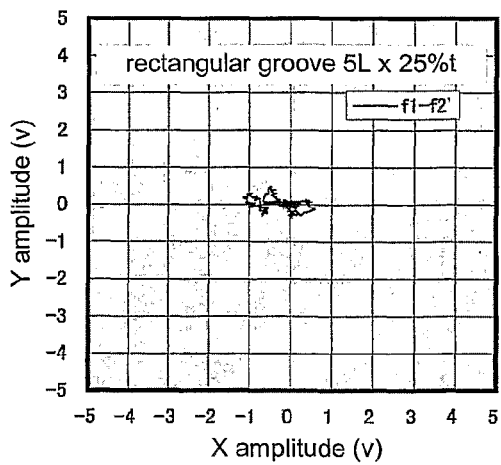
FIG. 11 shows other results of Example 3.
Figure 11:
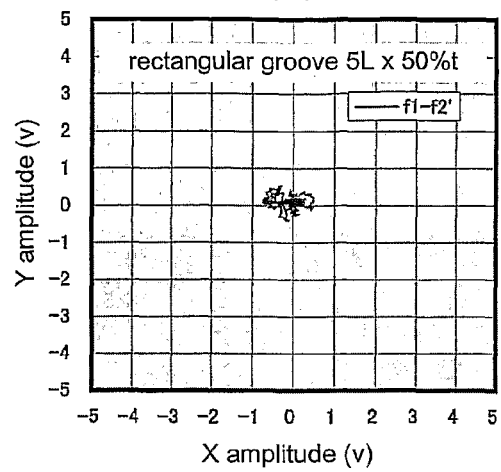
Figure 12:
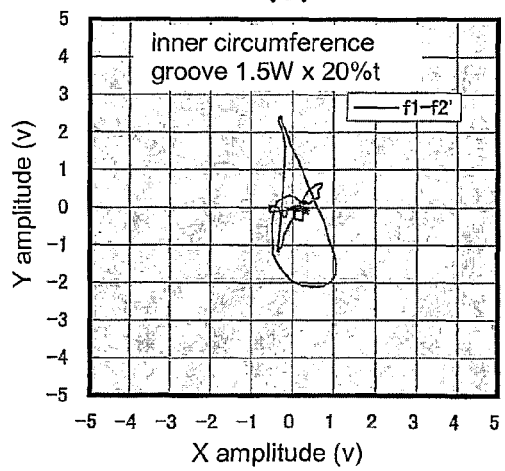
FIG. 12 shows other results of Example 3.
Figure 12:
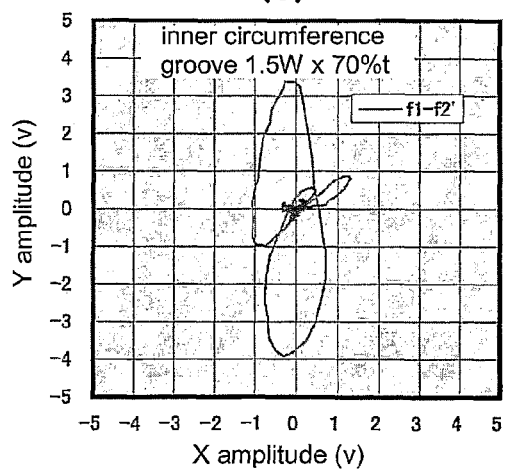
Figure 13:
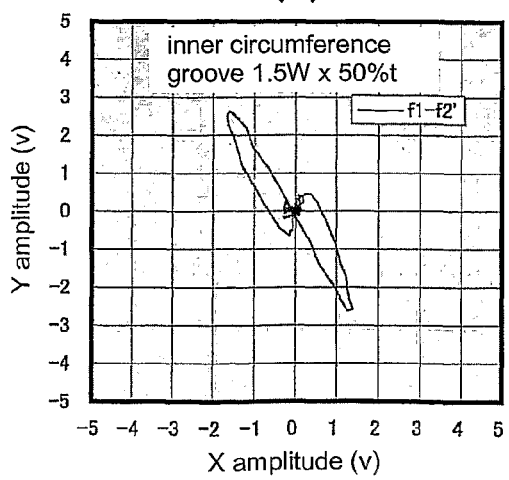
FIG. 13 shows other results of Example 3.
Figure 13:
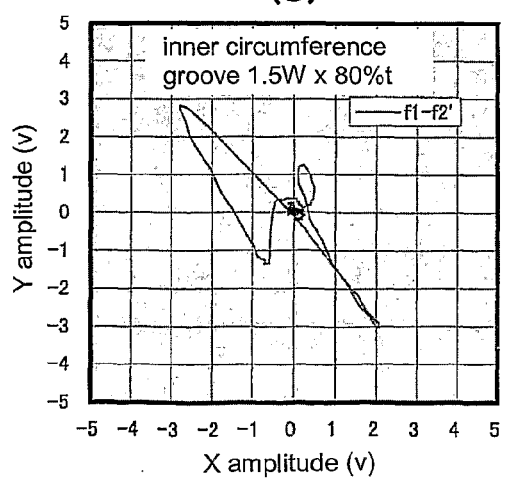

The signal of $f_2'$ operation was subtracted from the signal of $f_1$ operation ($f_1 - f_2'$) and flaws were inspected. This operation produced the Lissajous curves shown in FIG. 10 through FIG. 13. Graph (1) of FIG. 10 was obtained from a portion without flaw and graph (2) was obtained from the through hole 1 mm in diameter, graph (3) of FIG. 11 was obtained from the rectangular groove measuring 5 mm in width, 12.5 mm in length and 25% of the tube thickness in depth and graph (4) was obtained from the rectangular groove measuring 5 mm in width, 17.5 mm in length and 50% of the tube thickness in depth, graph (5) of FIG. 12 was obtained from the inner circumferential groove measuring 1.5 mm in width and 20% of the tube thickness in depth, graph (6) was obtained from the inner circumferential groove measuring 1.5 mm in width and 70% of the tube thickness in depth, graph (7) of FIG. 13 was obtained from the outer circumferential groove measuring 1.5 mm in width and 50% of the tube thickness in depth and graph (8) was obtained from the outer circumferential groove measuring 1.5 mm in width and 80% of the tube thickness in depth.

Comparison of the Lissajous curves (1) and (2) through (8) shows that flaws in the magnetic tube located in the portion of baffle provided outside were detected.

The present application claims priority based on Japanese Patent Applications 2009-057571, 2009-113360 and 2009-118402. The disclosures of the Japanese Patent Applications 2009-057571, 2009-113360 and 2009-118402 are incorporated by reference herein.

DESCRIPTION OF REFERENCE NUMERALS

1 Yoke
2 Permanent magnet
3 Permanent magnet
4 Permanent magnet
5 Detection coil
6 Inner excitation coil
7 Guide
8 Guide
9 Air intake hole
10 Air discharge hole

The invention claimed is:

1. An eddy current flaw detection probe, comprising:
a cylindrical yoke;
a plurality of detection coils disposed around the central portion of the cylindrical yoke in the direction of a cylindrical axis thereof;
first and second inner excitation coils disposed on both sides of the plurality of detection coils in the direction of the cylindrical axis, each of the first and second inner excitation coils inducing eddy current;
first and second permanent magnets disposed around the yoke on both sides of the first and second excitation coils in the direction of the cylindrical axis, the direction of magnetizations thereof being parallel to the radial direction of the yoke, magnetic poles on the cylindrical yoke side thereof being different from each other; and
wherein a signal applied to the excitation coils is also applied to the detection coils and the first and second excitation coils induce eddy current flowing in an opposite direction of eddy current induced by the plurality of the detection coils.

2. The eddy current flaw detection probe according to claim 1, wherein further comprising a third permanent magnet disposed between the cylindrical yoke and the plurality of detection coils, the first and second inner excitation coils, the direction of magnetization thereof being parallel to the direction of the axial direction of the yoke.

3. The eddy current flaw detection probe according to claim 1, wherein the magnetic flux density of the magnetic field generated by the permanent magnets is 1.5 tesla or higher in the central portion between the plurality of detection coils.

4. The eddy current flaw detection probe according to claim 2, wherein the magnetic flux density of the magnetic field generated by the permanent magnets is 1.5 tesla or higher in the central portion between the plurality of detection coils.

5. The eddy current flaw detection probe according to claim 1, wherein the cylindrical yoke comprises an air intake hole formed inside the cylindrical yoke and extending in the direction of the cylindrical axis and a plurality of air discharge holes formed to extend from the air intake hole to the surface of the cylindrical yoke in the radial direction of the cylindrical yoke.

6. The eddy current flaw detection probe according to claim 2, wherein the cylindrical yoke comprises an air intake hole formed inside the cylindrical yoke and extending in the direction of the cylindrical axis and a plurality of air discharge holes formed to extend from the air intake hole to the surface of the cylindrical yoke in the radial direction of the cylindrical yoke.

7. The eddy current flaw detection probe according to claim 3, wherein the cylindrical yoke comprises an air intake hole formed inside the cylindrical yoke and extending in the direction of the cylindrical axis and a plurality of air discharge holes formed to extend from the air intake hole to the surface of the cylindrical yoke in the radial direction of the cylindrical yoke.

8. A flaw detection method for a magnetic tube, wherein eddy current flaw detection on the inside of a magnetic tube is carried out by using an eddy current flaw detection probe, comprising:
a cylindrical yoke;

a plurality of detection coils disposed around the central portion of the cylindrical yoke in the direction of a cylindrical axis thereof;

first and second inner excitation coils disposed on both sides of the plurality of detection coils in the direction of the cylindrical axis, each of the first and second inner excitation coils inducing eddy current;

first and second permanent magnets disposed around the yoke on both sides of the first and second excitation coils in the direction of the cylindrical axis, the direction of magnetizations thereof being parallel to the radial direction of the yoke, magnetic poles on the cylindrical yoke side thereof being different from each other; and wherein a signal applied to the excitation coils is also applied to the detection coils and the first and second excitation coils induce eddy current flowing in an opposite direction of eddy current induced by the plurality of the detection coils.

9. The flaw detection method for a magnetic tube according to claim 8, wherein current including multiple frequencies is provided with the plurality of detection coils.

* * * * *